United States Patent [19]

Kabeta et al.

[11] Patent Number: 5,075,459

[45] Date of Patent: Dec. 24, 1991

[54] TREATMENT AGENT FOR INORGANIC SILICONACEOUS FILLER

[75] Inventors: Keiji Kabeta; Kiyoaki Syuto, both of Gunma, Japan

[73] Assignee: Toshiba Silicone Co., Ltd., Tokyo, Japan

[21] Appl. No.: 617,970

[22] Filed: Nov. 26, 1990

Related U.S. Application Data

[62] Division of Ser. No. 420,108, Oct. 11, 1989, abandoned.

[30] Foreign Application Priority Data

Oct. 17, 1988 [JP] Japan .................... 63-261232

[51] Int. Cl.$^5$ .................. C07D 303/02; C07F 7/04; C07F 7/10
[52] U.S. Cl. .................... 549/215; 556/414; 556/424; 528/25; 528/26; 522/99; 428/447451
[58] Field of Search ............ 549/215; 556/418, 424, 556/452, 414; 528/25, 26; 522/99; 428/447, 451

[56] References Cited

U.S. PATENT DOCUMENTS

| | | | |
|---|---|---|---|
| 3,922,466 | 11/1975 | Bell et al. | 549/214 |
| 4,551,541 | 11/1985 | Hanisch | 549/215 |
| 4,608,270 | 8/1986 | Varaprath | 556/424 |
| 4,652,662 | 3/1987 | von Au et al. | 556/424 |
| 4,697,009 | 9/1987 | Deschler et al. | 556/414 |
| 4,730,073 | 3/1988 | Takago et al. | 556/414 |
| 4,804,768 | 2/1989 | Quirk et al. | 549/215 |
| 4,876,363 | 10/1989 | Funahashi et al. | 549/215 |
| 4,889,768 | 12/1989 | Yokoshima et al. | 556/414 |

OTHER PUBLICATIONS

Agakishieva et al., Chem. Abst. vol. 82, 1/2/282, (1975).
T. A. Sladkova et al., Chem. Abst. vol. 63, 8395c, (1965).
S. J. Sodykh-Zade, Chem. Abst. vol. 61, 16087c, (1964).

*Primary Examiner*—Cecilia Shen
*Attorney, Agent, or Firm*—Flynn, Thiel, Boutell & Tanis

[57] ABSTRACT

A treatment agent for inorganic siliconaceous fillers has as its main ingredient an organosilicon compound of general fomrula (I):

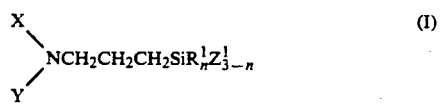

in which X represents a functional group selected from among $H_2NCH_2CH_2-$, $H_2NCH_2CH_2CH_2-$,

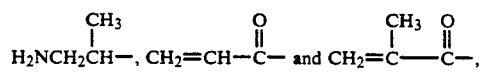

$Y^1$ is $CH_2=CHCH_2-$ or $-CH_2CH_2CH_2SiR_n^1Z_{3-n}^1$, $R^1$ is a substituted or nonsubstituted monovalent hydrocarbon group, $Z^1$ is an alkoxy group having 1-6 carbon atoms and n is an integer from 0-2, or of general formula (II):

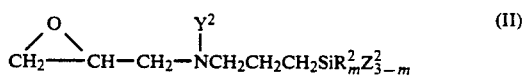

in which $Y^2$ is

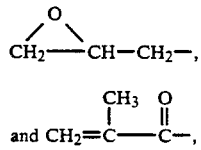

$-CH_2CH_2CH_2SiR_m^2Z_{3-m}^2$ or a substitutent or nonsubstituted monovalent hydrocarbon group, $Z^2$ is an alkoxy group having 1-6 carbon atoms and m is an integer from 0-2.

12 Claims, No Drawings

TREATMENT AGENT FOR INORGANIC SILICONACEOUS FILLER

This application is a division of U.S. Ser. No. 420,108, filed Oct. 11, 1989 is now abandoned.

TECHNICAL FIELD OF THE INVENTION

This invention relates to a treatment agent for inorganic siliconaceous filler and more specifically, relates to a treatment agent for inorganic siliconaceous filler which possesses effects which increase the compatibility, water resistance and adhesion with organic resins, of inorganic siliconaceous fillers which are used in various types of organic resins.

Inorganic siliconaceous fillers such as glass cloth and glass fiber are commonly used as one of the ingredients of laminated plates and structural materials. Normally, these articles are manufactured by impregnating thermocuring or thermoplastic resin into glass cloth or glass fiber followed by curing by heating.

For example, a thermocuring resin laminated plate may be manufactured by impregnating a thermocuring resin into a glass cloth, heating to form a prepreg in a semicured state and cutting to specified dimensions after which several plates are placed on top of each other and laminated by hot pressing. In addition, laminated copper plates which are used for printed wiring boards such as glass/epoxy laminated copper plates and glass/polyimide laminated copper plates, are manufactured by hot pressing superimposed sheets of copper foil on one or both sides.

From among the numerous elements which define the characteristics of glass fiber/epoxy resin compounds, the fiber/matrix interface is believed to be the most highly sensitive region within said compound. If the adhesion of the fiber to the resin in this region is weak, it will cause such defects as layer peeling, blistering and plateback, and these defects tremendously impair the function, reliability and manufacturing yield of printed circuit boards. Therefore, in more advanced multilayer circuit boards, it is necessary to improve the adhesion between the glass fiber and epoxy resin in order to achieve the higher level of product quality which is required since the circuit dimensions are smaller and the operating temperature is higher in such boards.

In order to improve the adhesion between the two phases of these materials and protect them from the effects of moisture, it is a common measure to use a bonding agent which improves the adhesion to the glass fiber surface of epoxy resins and other resins. Examples of commonly used bonding agents include 3-aminopropyltriethoxysilane and 3-glycidoxypropyltrimethoxysilane. Although it is clear that there is a strong adhesion between the resin components when silanes, especially the amino-substituted silanes and glycidoxy-substituted silanes mentioned above are used, these silane compounds still remain inadequate with respect to improving the adhesion between the resin and the glass fiber plate.

OBJECT OF THE PRESENT INVENTION

An object of this invention is to provide a new treatment agent for inorganic siliconaceous filler which results in remarkably improved adhesion between the inorganic siliconaceous filler and the organic resin, thereby making it suitable for more advanced compound applications.

SUMMARY OF THE INVENTION

As a result of earnest studies in order to obtain a treatment agent for inorganic siliconaceous fillers as described above, the inventors were able to complete the present invention by discovering a treatment agent for inorganic siliconaceous fillers which has as its main ingredient an organosilicon compound of general formula (I):

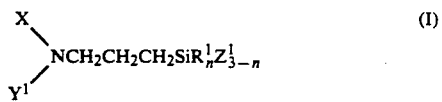

in which X represents a functional group selected from among $H_2NCH_2CH_2-$, $H_2NCH_2CH_2CH_2-$,

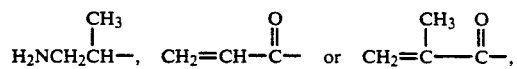

$Y^1$ represents $CH_2=CHCH_2-$ or $-CH_2CH_2CH_2SiR_n^1Z_{3-n}^1$, $R^1$ is a substituted or nonsubstituted monovalent hydrocarbon group, $Z^1$ is an alkoxy group having 1–6 carbon atoms and n is an integer from 0–2, or general formula (II):

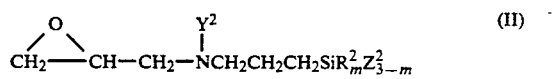

in which $Y^2$ is 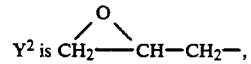

$-CH_2CH_2CH_2SiR_m^2Z_{3-m}^2$ or a substituted or nonsubstituted monovalent hydrocarbon group, $R^2$ is a substituted or nonsubstituted monovalent hydrocarbon group, $Z^2$ is an alkoxy group having 1–6 carbon atoms and m is an integer from 0–2.

In other words, this invention relates to a treatment agent for inorganic siliconaceous fillers which yields tremendously improved properties for applications of more advanced compounds.

DETAILED DESCRIPTION

Examples of organosilicon compounds of general formula (I) or (II) of the present invention include N,N-bis{3-(methyldimethoxysilyl)propyl}ethylenediamine, N,N-bis{3-(trimethoxysilyl)propyl}propylenediamine, N-allyl-N-{3-(trimethoxysilyl)propyl}ethylenediamine, N-allyl-N-{3-(methyldimethoxysilyl)propyl} propylenediamine, N-glycidyl-N,N-bis{3-(methyldimethoxysilyl)propyl}amine, N-glycidyl-N,N-bis{3-(trimethoxysilyl)propyl}amine, N-glycidyl-N-allyl-N-{3-(dimethylethoxysilyl)propyl}amine, N-glycidyl-N-allyl-N-{3-(trimethoxysilyl)propyl}amine, N,N-diglycidyl-N-{3-(trimethoxysilyl)propyl}amine, N-glycidyl-N-ethyl-N-{3-(trimethoxysilyl)propyl}amine, N-glycidyl-N-phenyl-N-{3-(trimethoxysilyl)propyl}amine, N,N-bis{3-(methyldiethoxysilyl)propyl}methacrylamide, N,N-bis{3-(dimethylethoxysilyl)propyl}methacrylamide, N,N-bis{3-(trimethoxysilyl)propyl}methacrylamide, N-allyl-N-{3-methyldiethoxysilyl)propyl}methacrylamide, and N-allyl-N-(3-trimethoxysilyl)- propylacrylamide. In addition, two or more types of these compounds can be used in a mixture.

These compounds can be prepared according to the following reactions.

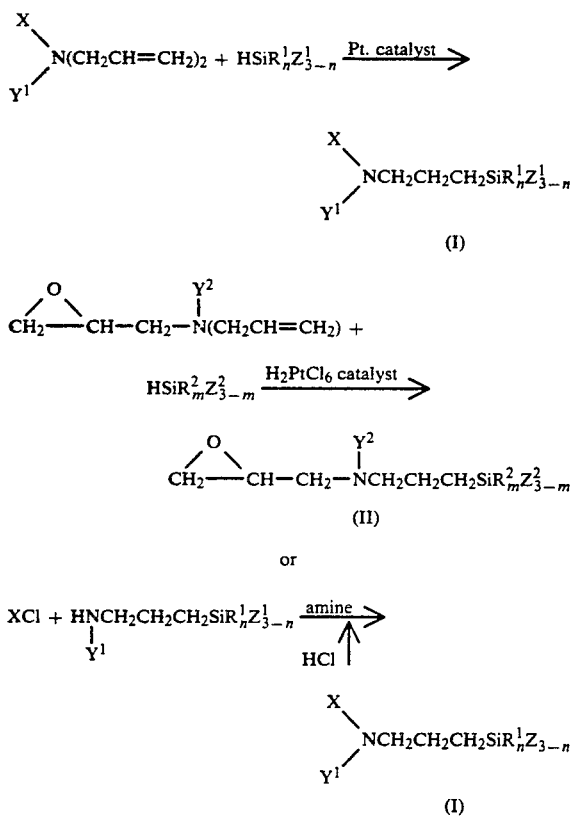

The following provides descriptions of the above reactions to produce the compounds of general formulas I and II.

An explanation will first be given regarding the reaction of the nitrogen-containing compound and the silane compound in the first two reactions. The catalyst that is used in this reaction is a catalyst that is commonly used in so-called hydrosilation reactions. Although examples of this catalyst include transition metals such as platinum, palladium, nickel, cobalt and ruthenium, as well as their complexes, platinum metals and complexes such as platinum black and chloroplatinic acid are preferable as they are able to result in a reduction in the reaction time as well as resulting in a high yield.

The amount of catalyst is preferably 0.001–5.0 parts by weight per 100 parts by weight of the nitrogen-containing compound with 0.01–1.0 parts by weight being more preferable. When the amount of catalyst added is less than 0.001 parts by weight, the reaction speed is insufficient and even if the catalyst is added in excess of 5.0 parts by weight, not only will there not be any observed improvement in reaction speed, but this is also not preferable in economic terms.

The prepared mole ratio of the silane compound with respect to the nitrogen-containing compound is roughly 2 moles, with a range of 2.0–3.0 being preferable in terms of practicality. Although the reaction can be carried out within a hydrosilation reaction temperature range of −30° to 150° C., the reaction is normally carried out within a more preferable range of 10° to 110° C. Although the reaction is normally carried out at atmospheric pressure, the pressure may be increased or decreased if necessary.

In addition, although the use of solvents at the time of reaction is not required, the use of a solvent to improve the solubility of the catalyst or control the temperature is allowable. Examples of such solvents include hydrocarbon-type solvents such as toluene, xylene, cyclohexane, n-hexane, n-heptane, naphtha, mineral spirit or petroleum benzine, halogenated hydrocarbon-type solvents such as chloroform, carbon tetrachloride, trichloroethylene, perchloroethylene or 1,1,1-trichloroethane, ether-type solvents such as ethyl ether, tetrahydrofuran or ethylene glycol diethyl ether, ester-type solvents such as ethyl acetate, butyl acetate or amyl acetate, ketone-type solvents such as acetone, methyl ethyl ketone or methyl isobutyl ketone, and aprotic polar solvents such as methylformamide or dimethylacetoamide.

Since reaction time varies according to the raw materials used, catalyst as well as solvent and reaction temperature, there are no limitations on this parameter in particular. However, reaction conditions are normally set so that the reaction is completed within 0.5 to 6 hours. The reaction is carried out by ordinary methods.

As an example, a method is employed in which a mixture of N,N-diallyl(meth)acrylamide and catalyst is heated to the specified temperature while stirring followed by dropping in the silane compound.

Since the compound is obtained as the result of a reaction of high selectivity, purification of the compound can be performed with currently known methods such as distillation, gas chromatography separation, liquid chromatography separation or column chromatography.

In order to increase the stability of the raw materials and products during the reaction and at the time of purification, the prior addition of known and suitable polymerization inhibitors and oxidation inhibitors is allowable as a routine procedure.

The following provides an explanation of the third reaction between the chloride-containing compound and the silane compound. In this reaction, since hydrogen chloride is formed, a dehydrochlorination agent is required. Although the amino group-containing silane compound can be used in excess for this purpose, more typically, another amine which does not react with the chloride-containing compound is added to the system. Examples of such an amine include pyridine, triethylamine, tributylamine and N-methylmorpholine. The amount of this amine that is added must be equal to or greater than the amount required to neutralize the hydrogen chloride that is produced as a by-product of the reaction. Typically, 1.0–1.5 equivalents of the amine is used with respect to the chloride-containing compound. If more than this amount is used, the reaction will be slowed and the reaction mixture will become too basic, resulting in the disadvantage of the stability of the products being decreased.

The prepared mole amount of the silane compound with respect to the chloride-containing compound is roughly 1.0 equivalents, and more preferably, 0.95–1.05 equivalents. If less than 0.95 equivalents of the silane compound is used, there will be an excessive amount of the unreacted chloride-containing compound remaining. Conversely, if more than 1.05 equivalents are added, a large amount of the silane compound will remain unreacted making this disadvantageous in economic terms. However, when using the silane compound as a dehydrochlorination agent as described above, it is only natural that the prepared mole ratio of silane to the chloride-containing compound be according to the amount of the amine added separately to function as the dehydrochlorination agent. In other words, since it is preferable that the total amount of amine in the reaction mixture be 2.0-2.5 equivalents with respect to the chloride-containing compound, it is preferable that the silane compound be prepared in an amount that results when the amount of amine that is actually added to serve as the dehydrochlorination agent is subtracted from the above amount.

Although this reaction is typically achieved by dropping the chloride-containing compound into a solution of the silane compound indicated in formula (5) and the amine used for dehydrochlorination, the use of a solvent is allowed to facilitate temperature control or make stirring easier. Examples of this solvent include hydrocarbon-type solvents such as toluene, xylene, cyclohexane, n-hexane, n-heptane, naphtha, mineral spirit or petroleum benzine, halogenated hydrocarbon-type solvents such as chloroform, carbon tetrachloride, trichloroethylene, perchloroethylene or 1,1,1-trichloroethane, ether-type solvents such as ethyl ether, tetrahydrofuran or ethylene glycol diethyl ether, ester-type solvents such as ethyl acetate, butyl acetate or amyl acetate, and aprotic polar solvents such as dimethylformamide or dimethylacetoamide.

Since the reaction time varies according to the raw materials used, catalyst, as well as the solvent and reaction temperature, there are no limitations on this parameter in particular. However, reaction conditions are typically set so that the reaction is completed within 0.5 to 6 hours.

After the reaction is completed and the hydrochloride of the amine is removed using by filtration or washing, the compound can be purified into the target substance by using known purification procedures similar to those of the previous method. In addition, the prior addition of polymerization inhibitors and oxidation inhibitors similar to those of the previous method during the reaction and at the time of purification is allowed as a routine procedure.

Further, it is also possible to use other alkoxysilanes such as methyltrimethoxysilane, -glycidoxypropyltrimethoxysilane and -aminopropyltrimethoxysilane as additives with the above-described organosilicon compounds as the main ingredient.

The treatment agent for inorganic siliconaceous fillers of this invention has an organosilicon compound of general formulae (I) and/or (II) as its main ingredient. Although it may be used as is, it also may be used dissolved in an organic solvent such as water, hydrocarbon type solvents such as toluene, xylene, cyclohexane, n-hexane, n-heptane, naphtha, mineral spirit and petroleum benzine, halogenated hydrocarbon-type solvents such as chloroform, carbon tetrachloride, trichloroethylene, perchloroethylene and 1,1,1-trichloroethane, ether-type solvents such as ethyl ether, tetrahydrofuran and ethylene glycol diethyl ether, ester-type solvents such as ethyl acetate, butyl acetate and amyl acetate, ketone-type solvents such as acetone, methyl ethyl ketone and methylisopropyl ketone, alcohol-type solvents such as methanol, ethanol, isopropanol, butanol, 2-methoxyethanol, 2-ethoxyethanol, 2-butoxyethanol, ethylene glycol and propylene glycol, aprotic polar solvents such as dimethylformamide, dimethylacetoamide and dimethylsulfoxide, or organopolysiloxane-type solvents such as hexamethyldisiloxane and 1,1,3,3,5,5,7,7,9,9,-decamethylcyclopentasiloxane. The solvent may be one type of solvent or a mixture of two or more types of solvents.

In addition, the concentration of the organosilicon compound main ingredient of formulae (I) and (II) in the inorganic siliconaceous filler treatment agent varies according to the type of inorganic siliconaceous filler and its method of treatment and is adjusted in accordance with this.

Examples of inorganic siliconaceous fillers which are treated with the inorganic siliconaceous filler treatment agent of the present invention include glass cloth, glass fiber, silica, glass beads, asbestos and wollastonite. Its application may be extended to any components of glass cloth and glass fiber. For example, E glass, C glass and S glass, etc., are preferable, and particularly in printed wiring board applications, nonalkaline glass such as E glass is preferable. The glass cloth used in this invention may be woven in any manner such as a flat weave, twilled weave, Shushi weave or triaxial weave. In addition, woven materials having other fibers in addition to glass fiber, such as a blend of glass fiber and carbon fiber, a blend of glass fiber and organic fiber or a blend of glass fiber and ceramic fiber, may also be used.

The glass cloth used in this invention may be either glass cloth at the stage in which the binder required for scutching is adhered to the cloth, or glass cloth at the stage at which the binder has been removed.

The binder mentioned here refers to the general type of binders which are added in the glass fiber spinning process (generally referred to as primary binders), and the binder which is added to the longitudinal glass fibers in the glass cloth gluing process (generally referred to as secondary binders). Specific examples include starch, surface activating agents, lubricants, synthetic oils and acrylic polymers.

Although methods for removing the binder include burning (dry method) and washing (wet method), a dry method is normally employed in which the glass cloth is continuously treated in an oven at approximately 600° C., or treated in several runs in an oven at 350°-400° C.

Examples of the organic resin that are also used in this invention include thermocuring resins such as epoxy, phenol, melamine, unsaturated polyester, diallylphthalate, polyimide and furan resins, or thermoplastic resins such as polyethylene, polypropylene, polystyrene, polybutylene, polyvinyl chloride, polyvinylidene chloride, polytetrafluoroethylene, polytrifluoropropene, polyvinyl acetate, polyacrylonitrile, polymethylmethacrylate, polyamide, polycarbonate, polyethylene terephthalate, polybutylene terephthalate, cellulose acetate and polyformaldehyde resins.

Commonly known methods may be used for applying the inorganic siliconaceous filler treatment agent of this invention to the inorganic siliconaceous filler. For example, in the case of applying the agent to glass cloth, any arbitrary method, such as immersion, spraying or gasification, can be employed. When using the immersion method, the glass cloth is immersed in the inorganic siliconaceous filler treatment agent for several seconds to one minute and, after air drying, the glass cloth is dried by heating at 80°-180° C.

When applying the agent to particulate inorganic siliconaceous fillers, such as silica or glass beads, any arbitrary method, such as a dry method, wet method or spraying, can be used. When using a dry method, the inorganic siliconaceous filler is forcibly stirred in a Henshell mixer or V blender and treated with the inorganic siliconaceous filler treatment agent which has been added.

EXAMPLES

The following discussion provides a detailed description of the present invention through the use of examples. However, these examples do not limit the present invention in any manner.

EXAMPLES 1-8 AND COMPARATIVE EXAMPLE 1

Heat-cleaned glass cloth (205 g/m$^2$) was immersed for 30 minutes in an adjusted aqueous solution of 1 wt. % of N,N-bis(3-trimethoxysilylpropyl)ethylenediamine. The glass cloth was air dried for 30 minutes followed by drying by heating in an oven at 100° C. for 30 minutes. After thoroughly impregnating the treated glass cloth with an epoxy resin blended liquid consisting of 100 parts by weight of Epicoat #1001 (Yuka Shell Co., Ltd.), 4 parts by weight of dicyandiamide, 0.2 part by weight of benzyldimethylamine and 100 parts by weight of methylcellusorb, the glass cloth was attached to a mold form and air dried for 30 minutes. Following this, the prepreg was made by heating the mold form for 5 minutes in a hot air drier at 160° C. 10 of the prepregs were superimposed on each other and preheated in a 160° C. press for 4 minutes with contact pressure. Treatment was continued by pressurizing the prepregs (40 kg/cm$_2$) for 20 minutes at 160° C. and followed by heat treatment for 60 minutes at 150° C. for the after-curing process. The laminated plate that was thus obtained was cut into 10 cm×10 cm squares followed by the conducting of a pressure cooker test. In other words, the penetration of water into the interface regions of the test samples was accelerated by boiling the laminated plates for 30-60 minutes at 2 atm. This test is useful for confirming whether or not the completed laminated plates can withstand a humidity cycle.

As a result of visual examination of the plates, the degree of damage was classified into 5 classes (1: zero, 5: all) with respect to the degree of peeling which was clear, referred to as blistering or measling, between the glass fiber and the epoxy resin.

1.0 wt. % aqueous solutions were adjusted using the compounds indicated in Table 1 as the organosilicon compound. For the solution that did not use a treatment agent of the present invention, the glass fiber was treated, the epoxy resin laminated plate was made and the test was performed in the same manner as in Example 1 (Comparative Example 1). The results are summarized in Table 1.

TABLE 1

| Example | Structural Formula of Compound | Results 1 | 2 | 3 | 4 | 5 |
|---|---|---|---|---|---|---|
| 1 | H$_2$NCH$_2$CH$_2$N{CH$_2$CH$_2$CH$_2$Si(OMe)$_3$}$_2$ | O | | | | |
| 2 | H$_2$NCH$_2$CH$_2$N{CH$_2$CH$_2$CH$_2$Si(OMe)$_2$}$_2$ with Me substituent | O | | | | |
| 3 | H$_2$NCH$_2$CH$_2$NCH$_2$CH$_2$CH$_2$Si(OMe)$_3$ with CH$_2$=CHCH$_2$ substituent | O | | | | |
| 4 | (epoxy)CH$_2$—CHCH$_2$N{CH$_2$CH$_2$CH$_2$Si(OMe)$_3$}$_2$ | O | | | | |
| 5 | (epoxy)CH$_2$—CHCH$_2$NCH$_2$CH$_2$CH$_2$Si(OMe)$_3$ with CH$_2$=CHCH$_2$ substituent | O | | | | |
| 6 | {(epoxy)CH$_2$—CHCH$_2$}$_2$NCH$_2$CH$_2$CH$_2$Si(OMe)$_3$ | O | | | | |
| 7 | CH$_2$=C(CH$_3$)—C(=O)—N{CH$_2$CH$_2$CH$_2$Si(OMe)$_3$}$_2$ | O | | | | |
| 8 | CH$_2$=C(CH$_3$)—C(=O)—N(CH$_2$—CH=CH$_2$)CH$_2$CH$_2$CH$_2$Si(OMe)$_3$ | O | | | | |
| Comparative Example 1 | (epoxy)CH$_2$—CHCH$_2$OCH$_2$CH$_2$CH$_2$Si(OMe)$_3$ | | | | | O |

EXAMPLES 9-11 AND COMPARATIVE EXAMPLE 2

The treated glass cloth prepared in Example 1 was impregnated with polyester resin (a blend of 100 parts by weight of Ester GA20 (Mitsui Toatsu Co., Ltd.) and 1.5 parts by weight of benzoylperoxide). 10 pieces of the impregnated glass cloth were superimposed on each other and cured for 1 hour with contact pressure at 100°

C. Then, the plates were after-cured for an additional 4 hours. A pressure cooker test as described previously was then conducted using these polyester resin laminated plates. The results are summarized in Table 2.

In addition, a treated glass cloth, other than those which used the compounds indicated in Table 2 for the organosilicon compound, was prepared and polyester resin laminated plates were made using this cloth and tests were conducted in the same manner as in Examples 9–11. Those results are summarized in Table 2.

TABLE 2

| | Structural Formula of Compound | Results 1 | 2 | 3 | 4 | 5 |
|---|---|---|---|---|---|---|
| Example 9 | $CH_2{=}C(CH_3){-}C(O){-}N\{CH_2CH_2CH_2Si(OMe)_3\}_2$ | ◯ | | | | |
| 10 | $CH_2{=}C(CH_3){-}C(O){-}N\{CH_2CH_2CH_2Si(OMe)_2Me\}_2$ | ◯ | | | | |
| 11 | $CH_2{=}C(CH_3){-}C(O){-}N(CH_2{-}CH{=}CH_2)CH_2CH_2CH_2Si(OMe)_3$ | ◯ | | | | |
| Comparative Example 2 | $CH_2{=}C(CH_3){-}C(O){-}OCH_2CH_2CH_2Si(OMe)_3$ | ◯ | | | | |

The inorganic siliconaceous filler treatment agent of this invention, which has an organosilicon compound of general formulae (I) and/or (II) for its main ingredient, strengthens the bonding of inorganic siliconaceous fillers with various types of organic resins, and exhibits improved water resistance and adhesion in comparison to conventionally used organosilicon compounds.

Based on the above, the inorganic siliconaceous filler treatment agent of the present invention is effective as a treatment agent of organic siliconaceous materials which are used in various types of compound materials, and is able to be suitably used in these types of applications.

What is claimed is:

1. In an article containing an organic resin and an inorganic siliconaceous filler, the improvement comprising said siliconaceous filler having a treatment agent applied thereto, said treatment agent having as its main ingredient an organosilicon compound of formula (I):

$$\begin{matrix} X \\ \phantom{X}\diagdown \\ \phantom{XXX}NCH_2CH_2CH_2SiR^1_nZ^1_{3-n} \\ \phantom{X}\diagup \\ Y \end{matrix} \quad (I)$$

in which X represents a functional group selected from among $H_2NCH_2CH_2{-}$, $H_2NCH_2CH_2CH_2{-}$,

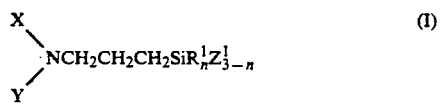

and $Y^1$ is $CH_2{=}CHCH_2{-}$ or $-CH_2CH_2CH_2SiR^1_nZ^1_{3-n}$, $R^1$ is a methyl group, $Z^1$ is an alkoxy group having 1–6 carbon atoms and n is an integer from 0–2.

2. In an article containing an organic resin and an inorganic siliconaceous filler, the improvement comprising said siliconaceous filler having a treatment agent applied thereto, said treatment agent having as its main ingredient an organosilicon compound of formula (II):

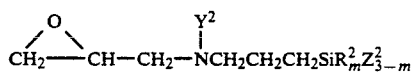

(II)

in which $Y_2$ is

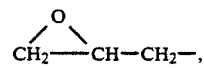

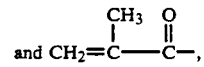

$-CH_2CH_2CH_2SiR^2_mZ^2_{3-m}$, a phenyl group or an ethyl group, $R^2$ is a methyl group, $Z^2$ is an alkoxy group having 1–6 carbon atoms and m is an integer from 0–2.

3. The article of claim 1, wherein said organosilicon compound is $H_2NCH_2CH_2N\{CH_2CH_2CH_2Si(OMe)_3\}_2$.

4. The article of claim 1, wherein said organosilicon compound is

5. The article of claim 1, wherein said organosilicon compound is

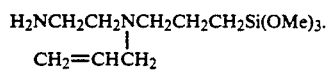

6. The article of claim 2, wherein said organosilicon compound is

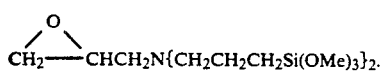

7. The article of claim 2, wherein said organosilicon compound is

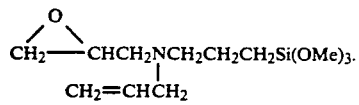

8. The article of claim 2, wherein said organosilicon compound is

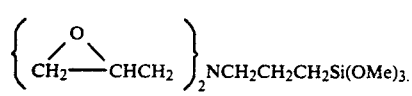

9. The article of claim 1, wherein said organosilicon compound is

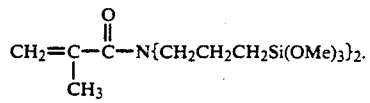

10. The article of claim 1, wherein said organosilicon compound is

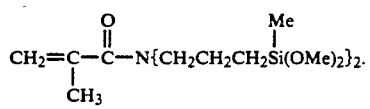

11. The article of claim 1, wherein said organosilicon compound is

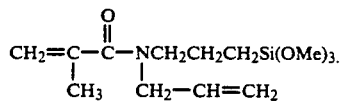

12. The article of claim 1, wherein said resin is an epoxy resin.

* * * * *

UNITED STATES PATENT AND TRADEMARK OFFICE
CERTIFICATE OF CORRECTION

PATENT NO. : 5 075 459

DATED : December 24, 1991

INVENTOR(S) : Keiji KABETA et al

It is certified that error appears in the above-identified patent and that said Letters Patent is hereby corrected as shown below:

On the title page, at item [57], line 4; change
"fomrula" to ---formula---.

On the title page, at item [57], line 9; change
"$-CH_2CH_2CH_2SiR_n^{1}Z_{3-n}^{1}$" to
--- $-CH_2CH_2CH_2SiR_n^{1}Z_{3-n}^{1}$ ---.

On the title page, at item [57], line 17; delete the following:

"and 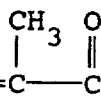,"

UNITED STATES PATENT AND TRADEMARK OFFICE
CERTIFICATE OF CORRECTION

PATENT NO. : 5 075 459
DATED : December 24, 1991
INVENTOR(S) : Keiji KABETA et al It is certified that error appears in the above-identified patent and that said Letters Patent is hereby corrected as shown below:

On the title page, at item [57], line 18; change

"$-CH_2CH_2CH_2SiR_m^2Z_{3-m}^2$"   to

--- $-CH_2CH_2CH_2SiR_m^2Z_{3-m}^2$ ---.

On the title page, at item [57] line 18; change "substitutent" to --substituted--.

Column 10, line 1; change "$-CH_2CH_2CH_2SiR_n^1Z_{3-n}^1$"

to --- $CH_2CH_2CH_2SiR_n^1Z_{3-n}^1$ ---.

UNITED STATES PATENT AND TRADEMARK OFFICE
CERTIFICATE OF CORRECTION

PATENT NO. : 5 075 459
DATED : December 24, 1991
INVENTOR(S) : Keiji KABETA et al It is certified that error appears in the above-identified patent and that said Letters Patent is hereby corrected as shown below:

Column 10, line 45; delete the following:

"and 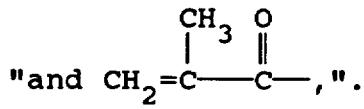,".

Column 10, line 47; change "$-CH_2CH_2CH_2SiR_m^2Z_{3-m}^2$"

to ---  ---.

Signed and Sealed this

Twenty-fourth Day of August, 1993

*Attest:*

BRUCE LEHMAN

*Attesting Officer*  Commissioner of Patents and Trademarks